US010077355B2

(12) United States Patent
Mundra et al.

(10) Patent No.: US 10,077,355 B2
(45) Date of Patent: Sep. 18, 2018

(54) PLASTICIZER COMPOSITIONS AND METHODS FOR MAKING PLASTICIZER COMPOSITIONS

(71) Applicant: Dow Global Technologies LLC, Midland, MI (US)

(72) Inventors: Manish Mundra, Collegeville, PA (US); Abhijit Ghosh-Dastidar, East Brunswick, NJ (US); Robert F. Eaton, Belle Mead, NJ (US); Lin Fu, Naperville, IL (US); Robert M. Campbell, Midland, MI (US); Bruce M. Bell, Higgins Lake, MI (US)

(73) Assignee: Dow Global Technologies LLC, Midland, MI (US)

( * ) Notice: Subject to any disclaimer, the term of this patent is extended or adjusted under 35 U.S.C. 154(b) by 23 days.

(21) Appl. No.: 15/335,532

(22) Filed: Oct. 27, 2016

(65) Prior Publication Data

US 2017/0088695 A1    Mar. 30, 2017

Related U.S. Application Data

(62) Division of application No. 14/370,883, filed as application No. PCT/US2013/023362 on Jan. 28, 2013, now abandoned.

(60) Provisional application No. 61/596,432, filed on Feb. 8, 2012.

(51) Int. Cl.
*C08K 5/1515* (2006.01)
*C08K 9/02* (2006.01)
*C07D 301/32* (2006.01)

(52) U.S. Cl.
CPC .............. *C08K 9/02* (2013.01); *C07D 301/32* (2013.01); *C08K 5/1515* (2013.01)

(58) Field of Classification Search
CPC ..................... C08K 5/1515; C07D 301/32
See application file for complete search history.

(56) References Cited

U.S. PATENT DOCUMENTS

| | | |
|---|---|---|
| 2,397,592 A | 4/1946 | Blades |
| 2,403,215 A | 7/1946 | Foster |
| 2,458,484 A | 1/1949 | Terry et al. |
| 2,500,918 A | 3/1950 | Rueter et al. |
| 2,618,622 A | 11/1952 | Grummit et al. |
| 2,666,752 A | 1/1954 | Grummit et al. |
| 3,138,566 A | 6/1964 | Arnold |
| 3,409,580 A | 11/1968 | Alzner |
| 3,639,318 A | 2/1972 | Tijunelis et al. |
| 3,668,091 A | 6/1972 | French et al. |
| 3,712,875 A | 1/1973 | Tijunelis |
| 3,778,465 A | 12/1973 | Bamstorf |
| 3,780,140 A | 12/1973 | Hammer |
| 3,868,341 A | 2/1975 | Sauer et al. |
| 3,872,187 A | 3/1975 | Fath |
| 3,891,694 A | 6/1975 | Mills et al. |
| 4,083,816 A | 4/1978 | Frankel et al. |
| 4,346,145 A | 8/1982 | Choi et al. |
| 4,421,886 A | 12/1983 | Worschech et al. |
| 4,426,477 A | 1/1984 | Yasumatsu et al. |
| 4,556,694 A | 12/1985 | Wallace |
| 4,605,694 A | 8/1986 | Walker |
| 4,612,192 A | 9/1986 | Scheuffgen et al. |
| 4,613,533 A | 9/1986 | Loomis et al. |
| 4,627,993 A | 12/1986 | Loomis |
| 4,670,494 A | 6/1987 | Semenza, Jr. |
| 4,689,429 A * | 8/1987 | Mertz ................... C07C 69/42 524/314 |
| 4,857,600 A | 8/1989 | Gross et al. |
| 5,225,108 A | 7/1993 | Bae et al. |
| 5,227,417 A | 7/1993 | Kroushl, III |
| 5,246,783 A | 9/1993 | Spenadel et al. |
| 5,270,366 A | 12/1993 | Hein |
| 5,278,236 A | 1/1994 | Case et al. |
| 5,430,108 A | 7/1995 | Schlosberg et al. |
| 5,454,806 A | 10/1995 | Shinonome |
| 5,464,903 A | 11/1995 | Hofmann |
| 5,466,267 A | 11/1995 | Baillargeon et al. |
| 5,575,965 A | 11/1996 | Caronia et al. |
| 5,736,605 A | 4/1998 | Oshima |
| 5,756,570 A | 5/1998 | Hoch et al. |
| 5,886,072 A | 3/1999 | Linsky et al. |
| 6,063,846 A | 5/2000 | Weng et al. |
| 6,114,425 A | 9/2000 | Day et al. |

(Continued)

FOREIGN PATENT DOCUMENTS

| | | |
|---|---|---|
| CA | 1188445 A1 | 6/1985 |
| CN | 1341681 A | 3/2002 |

(Continued)

OTHER PUBLICATIONS

CN 101376631 A, 03-2009m Derwent Ab.*
PCT/US2010/050699 International Search Report and Written Opinion, dated Nov. 8, 2010.
PCT/US2011/035143 International Search Report and Written Opinion, dated Aug. 30, 2011.
PCT/US2011/041557 International Search Report and Written Opinion, dated Sep. 7, 2011.
PCT/US2011/045653 International Search Report and Written Opinion, dated Oct. 8, 2011.
PCT/US2012/043740 International Search Report and Written Opinion, dated Jan. 28, 2013.

(Continued)

*Primary Examiner* — Satya Sastri

(57) ABSTRACT

The present disclosure is directed to a plasticizer composition, polymeric compositions containing the plasticizer composition, and conductors coated with the polymeric composition. The plasticizer composition includes a first plasticizer comprising epoxidized fatty acid alkyl esters and a second plasticizer comprising an epoxidized natural oil. The plasticizer composition, first plasticizer, and/or second plasticizer can undergo one or more color-reducing treatment processes, such as distillation, filtration, and/or peroxide treatment.

6 Claims, No Drawings

(56) References Cited

U.S. PATENT DOCUMENTS

| | | | |
|---|---|---|---|
| 6,274,750 B1 | 8/2001 | Sato et al. | |
| 6,417,260 B1 | 7/2002 | Weng et al. | |
| 6,437,170 B1 | 8/2002 | Thil et al. | |
| 6,451,958 B1 | 9/2002 | Fan et al. | |
| 6,495,033 B1 | 12/2002 | Talboom | |
| 6,496,629 B2 | 12/2002 | Ma et al. | |
| 6,608,142 B1 | 8/2003 | Weng et al. | |
| 6,706,815 B2 | 3/2004 | Marchand et al. | |
| 6,714,707 B2 | 3/2004 | Rossi et al. | |
| 6,734,241 B1 | 5/2004 | Nielsen et al. | |
| 6,797,753 B2 | 9/2004 | Benecke et al. | |
| 6,849,694 B2 | 2/2005 | Hata | |
| 6,949,597 B2 | 9/2005 | Nielsen et al. | |
| 7,700,675 B2 | 4/2010 | Bueno de Almeida et al. | |
| 8,557,139 B2 * | 10/2013 | Eaton | C08K 5/1515 252/182.28 |
| 2002/0013396 A1 | 1/2002 | Benecke et al. | |
| 2004/0122159 A1 | 6/2004 | Mhetar et al. | |
| 2005/0090590 A1 | 4/2005 | Nielsen et al. | |
| 2005/0203230 A1 | 9/2005 | Kadakia et al. | |
| 2006/0025544 A1 | 2/2006 | Koube et al. | |
| 2006/0276575 A1 | 12/2006 | Hamaguchi et al. | |
| 2007/0100049 A1 | 5/2007 | Ishizuka | |
| 2007/0135562 A1 | 6/2007 | Freese et al. | |
| 2008/0200595 A1 | 8/2008 | Hinault et al. | |
| 2008/0227993 A1 | 9/2008 | Zuckerman | |
| 2009/0149585 A1 | 6/2009 | De Quadros Junior et al. | |
| 2009/0149586 A1 | 6/2009 | De Quadros Junior et al. | |
| 2009/0312478 A1 | 12/2009 | Hasegawa et al. | |
| 2010/0010127 A1 | 1/2010 | Barki et al. | |
| 2010/0256278 A1 | 10/2010 | Harada et al. | |
| 2011/0076502 A1 | 3/2011 | Chaudhary et al. | |
| 2011/0272174 A1 * | 11/2011 | Chaudhary | C08L 27/06 174/110 SR |
| 2013/0005937 A1 | 1/2013 | Cramail et al. | |

FOREIGN PATENT DOCUMENTS

| | | | |
|---|---|---|---|
| CN | 101108982 | | 1/2006 |
| CN | 101070510 | | 11/2007 |
| CN | 101376631 A | * | 3/2009 |
| CN | 101591588 A | | 12/2009 |
| CN | 101824193 A | | 9/2010 |
| CN | 101914219 A | | 12/2010 |
| EP | 0192961 A1 | | 9/1986 |
| EP | 0358179 A2 | | 3/1990 |
| EP | 0364717 A1 | | 4/1990 |
| EP | 0 393 813 A1 | | 10/1990 |
| EP | 0473915 A1 | | 3/1992 |
| EP | 0565984 A1 | | 10/1993 |
| EP | 0986606 A1 | | 3/2000 |
| EP | 1218443 A1 | | 7/2002 |
| EP | 1361039 A1 | | 11/2003 |
| EP | 1624014 A1 | | 2/2006 |
| EP | 2070977 A2 | | 6/2009 |
| EP | 2245089 A1 | | 11/2010 |
| FR | 1437722 A | | 5/1966 |
| GB | 499931 A | | 1/1939 |
| GB | 790314 A | | 2/1958 |
| GB | 910543 A | | 11/1962 |
| GB | 934689 A | | 8/1963 |
| GB | 1022920 A | | 4/1964 |
| GB | 1102506 A | | 2/1968 |
| GB | 1341623 A | | 12/1973 |
| GB | 2155021 A | | 9/1985 |
| JP | S44-007131 | | 3/1969 |
| JP | S61-016950 | | 1/1986 |
| JP | 04-059851 B2 | | 2/1992 |
| JP | H04-085354 | | 3/1992 |
| JP | H04-261452 A | | 9/1992 |
| JP | 2000-319468 A | | 11/2000 |
| JP | 2003-064233 A | | 3/2003 |
| JP | 2003-297149 A | | 10/2003 |
| JP | 2004311064 A | | 11/2004 |
| JP | 2010-042669 A | | 2/2010 |
| WO | 9730115 A1 | | 8/1997 |
| WO | 0114466 A1 | | 3/2001 |
| WO | 0198404 A2 | | 12/2001 |
| WO | 2004052977 A1 | | 6/2004 |
| WO | 2007006489 A1 | | 1/2007 |
| WO | 2008081330 A1 | | 7/2008 |
| WO | 2008081332 A1 | | 7/2008 |
| WO | 2008122364 A1 | | 10/2008 |
| WO | 2009102877 A1 | | 8/2009 |
| WO | WO 2009102877 A1 * | 8/2009 | ........... C08K 5/1515 |
| WO | 2011/041380 A1 | | 4/2011 |
| WO | 2011/041388 A1 | | 4/2011 |
| WO | 2011041372 A1 | | 4/2011 |
| WO | 2011041380 A1 | | 4/2011 |
| WO | 2011041388 A1 | | 4/2011 |
| WO | 2013003225 A2 | | 1/2013 |

OTHER PUBLICATIONS

PCT/US2012/055070 International Search Report and Written Opinion, dated Dec. 10, 2012.
Danisco, Grindsted Soft-n-Safe brochure 2007/2008.
Barnicoat, C.R. 1945. Reactions and properties of annatto as a cheese colour. Part II. J. Dairy Res. 14: 59-63.
Bizzari, S.N. et al (2003), Plasticizers. CEH Marketing Research Report, 38-64, Retrieved from http://www.sriconsulting.com.
Campanella A. et al.; High Yield Epoxidation of Fatty Acid Methyl Esters with Performic Acid Generated In Situ; Chemical Engineering Journal, 144 (2008) 466-475 (Elsevier B.V.).
Chuanshang Cai, et al.; Studies on the Kinetics of In Situ Epoxidation of Vegetable Oils; Eur. J. Lipid Sci. Technol., 2008, 110, 341-346 (Wiley-VCH GmbH & Co. KGaA, Weinheim).
Corrigan, Brian Oil purification, filtration and reclamation, Iron Age (1947) 159(14).
Danisco, Grindsted Soft-n-Safe brochure pp. 1-8, 2007/2008.
Du G., et al., Catalytic Epoxidation of Methyl Linoleate, JAOCS, vol. 81, No. 4 (2004).
Freedman, F., Butterfield, R., and Pryde, E.H. Transesterification Kinetics of Soybean Oil. JAOCS, 63(10) p. 1375 (1986).
Gan, L. H., et al (1994) Epozidized esters of palm olein as plasticizers for poly (vinyl chloride). European Polymer Journal, 31(8), 719-724.
Greenspan, F. P. et al (1953) Epoxy fatty acid ester plasticizers. Indstrial and Engineering Chemistry, 445(12), 2722-2726.
Greenspan, F.P. et al (1956), Epoxy fatty acid ester plasticizers. Prepararion and properties, The Journal of the American Oil Chemists Society, 33, 391-394.
Grummitt O. and Fleming H. Acetylated Castor Oil Industrial and Engineering Chemistry, vol. 37, No. 5, May 1945, pp. 485-491.
Haas, Michael J. Improving the Economics of biodiesel production through the use of low value lipids as feedstocks: vegetable oil soapstock, Fuel Processing Technology 86 p. 1087-96 (2005).
Jensen, R.G. Purification of Triglycerides with an Aluminca Column, Lipids, 451-452 (1966).
Morgenstern, B. "Epoxidized Fatty Acid Esters as Plasticizers for PVC" dated Apr. 22, 2005.
Morgenstern, B. Epoxidized Fatty Acid Esters as Plasticizers for PVC, presented at the 7th Freiberg Polymer Conference, Apr. 21 and 22, 2005.
Morgenstern, B. Use of Modified Fatty Acid Esters as Plasticizers for PVC, dated Sep. 12, 2003.
Opposition to patent EP2245089, Dated Jan. 9, 2013.
Orellana-Coca et al., Lipase Mediated Simultaneous Esterification and Epoxidation of Oleic Acid for the Production of Alkylepoxystearates. Journal of Molecular Catalysis B: Enzymatic 44 (2007) 133-137.
Stuart, A et al., Polym. Bull. (2010) 65:589-598.
Rehberg, C. et. Al. Plasticizers from Lactic Esters and Biabasic Acids Ind. Eng. Chem., 1952, 44 (9), pp. 2191-2195.
Santacesaria E. et al.; A Biphasic Model Describing Soybean Oil Epoxidation with H2O2 in a Fed-Batch Reactor; Chemical Engineering Journal, vol. 173, Issue 1, Sep. 1, 2011, pp. 198-209 (Elsevier B.V.).

(56) References Cited

OTHER PUBLICATIONS

Senžana S. et al.; Kinetics of In Situ Epoxidation of Soybean Oil in Bulk Catalyzed by Ion Exchange Resin; Journal of the American Oil Chemists' Society, vol. 78, No. 7 (2001) 725-731 (AOCS Press).
Sheehan, J et al. "A Look Back at the U.S. Department of Energy's Aquatic Species Program: Biodiesel from Algae", National Renewable Energy Laboratory, Colorado, Jul. 1998, pp. 1-294.
Taylor, D. R. Proceedings of the World Conference on oilseed technology and utilization, Adsorptive Purification, American Oil Chemists Society, Champaing, 1992, p. 152-165.
Tekin A., and Hammond E. Factors Affecting the Electrical Resistivity of Soybean Oil, JAOCS, vol. 75(6) 1998.
XP002657062 Vertellus Performance Materials Inc.; Flexricin P-8 Technical Data Sheet, Nov. 2006.
XP002669860, Thomson Scientific, Mar. 13, 2009, London, GB.
PCT/ US2009/033935, International Preliminary Report on Patentability, dated Aug. 26, 2010.
PCT/US2009/033935 International Search Report and Written Opinion dated May 18, 2009.
PCT/US2010/050654 International Search Report and Written Opinion dated Nov. 9, 2010.
PCT/US2010/050676 International Search Report and Written Opinion dated Jan. 12, 2011.
PCT/US2010/050690 International Preliminary Report on Patentability, dated Jan. 12, 2012.
PCT/US2010/050690 International Search Report and Written Opinion, dated Aug. 2, 2011.
PCT/US2011/035143 International Search Report and Written Opinion, dated Aug. 26, 2011.
PCT/US2011/041557 International Preliminary Report on Patentability, dated Aug. 31, 2012.
PCT/US2011/041557 International Search Report and Written Opinion, dated Sep. 5, 2011.
PCT/US2011/045653 International Search Report and Written Opinion, dated Oct. 7, 2011.
PCT/US2012/043740 International Search Report and Written Opinion, dated Jan. 23, 2013.
PCT/US2012/055070 International Search Report and Written Opinion dated Dec. 3, 2012.
PCT/US2013/023362 International Search Report and Written Opinion, dated Mar. 28, 2013.
PCT/US2013/023362, International Preliminary Report on Patentability, dated Aug. 12, 2014.
PCT/ US2009/033935, International Preliminary Report on Patentability, dated May 27, 2009.
PCT/ US2009/033935, International Preliminary Report on Patentability, dated May 18, 2009.
PCT/US2010/050654 International Search Report and Written Opinion, dated Nov. 12, 2010.
PCT/US2010/050690 International Search Report and Written Opinion, dated Jan. 1, 2012.
PCT/US2010/050690 International Preliminary Report on Patentability, dated Jan. 24, 2012.

* cited by examiner

PLASTICIZER COMPOSITIONS AND METHODS FOR MAKING PLASTICIZER COMPOSITIONS

REFERENCE TO RELATED APPLICATIONS

This application is a divisional of U.S. patent application Ser. No. 14/370,883, which was a National Stage of International Application No. PCT/US2013/023362 filed on Jan. 28, 2013, which claimed priority from U.S. Provisional Patent Application No. 61/596,432 filed on Feb. 8, 2012 entitled "PLASTICIZER COMPOSITIONS AND METHODS FOR MAKING PLASTICIZER COMPOSITIONS," the teachings of each of which are incorporated by reference herein, as if reproduced in full hereinbelow.

FIELD

Various embodiments of the present invention relate to plasticizers derived from natural oils (e.g., oils derived from biological sources). Other aspects of the invention concern a process for producing such plasticizers.

INTRODUCTION

Plasticizers are compounds or mixtures of compounds that are added to polymer resins to impart softness and flexibility. Phthalic acid diesters (also known as "phthalates") are known plasticizers in many flexible polymer products, such as polymer products formed from polyvinyl chloride ("PVC") and other vinyl polymers. Examples of common phthalate plasticizers include di-isononyl phthalate, diallyl phthalate, di-2-ethylhexyl-phthalate, dioctyl phthalate, and diisodecyl phthalate. Other common plasticizers, used for high temperature applications, are trimellitates and adipic polyesters. Mixtures of plasticizers are often used to obtain optimum properties.

Phthalate plasticizers have recently come under intense scrutiny by public interest groups that are concerned about the negative environmental impact of phthalates and potential adverse health effects in humans (especially children) exposed to phthalates.

Epoxidized methyl ester of soybean oil (e.g., epoxidized fatty acid methyl ester, or "eFAME") can be used as a plasticizer for polyvinyl chloride ("PVC") and other polymers (natural rubber, acrylate, etc.) or alternately, it can be used as a primary or secondary plasticizer in a plasticizer blend (such as with epoxidized soybean oil ("ESO")). However, eFAME often contains various impurities that may cause color in plasticized compositions. Accordingly, improvements in such plasticizers are desired.

SUMMARY

One embodiment is a plasticizer composition comprising: a first plasticizer comprising epoxidized fatty acid alkyl esters; and a second plasticizer comprising an epoxidized natural oil, wherein said first plasticizer comprises fatty acid dimers in a concentration of less than 0.1 weight percent based on the entire weight of said first plasticizer.

Another embodiment is a method for producing a treated plasticizer, said method comprising:
(a) combining a first plasticizer and a second plasticizer to thereby form a plasticizer composition, wherein said first plasticizer comprises epoxidized fatty acid alkyl esters, wherein said second plasticizer comprises an epoxidized natural oil; and
(b) subjecting said first plasticizer, said second plasticizer, and/or said plasticizer composition to one or more color-reducing treatment processes to thereby produce said treated plasticizer,
wherein said color-reducing treatment process is selected from the group consisting of:
(i) contacting at least a portion of said first plasticizer, said second plasticizer, and/or said plasticizer composition with a peroxide;
(ii) filtering at least a portion of said first plasticizer, said second plasticizer, and/or said plasticizer composition;
(iii) distilling at least a portion of said first plasticizer prior to said combining of step (a); and
(iv) mixtures of two or more thereof.

DETAILED DESCRIPTION

Various embodiments of the present invention concern plasticizers derived from natural oils. In one or more embodiments, the plasticizer includes an epoxidized natural oil ("eNO"). Additionally, the plasticizer includes a natural oil that has been epoxidized and esterified forming epoxidized fatty acid alkyl esters ("eFAAE"). In preparing such plasticizers, the eNO, eFAAE, and/or combinations thereof can undergo one or more color treatment processes. Such plasticizers can be employed with a variety of polymeric resins and in the making of various articles of manufacture.

Plasticizer

The present disclosure provides a plasticizer composed of an epoxidized fatty acid alkyl ester and an epoxidized natural oil. A plasticizer is a substance that can lower the modulus and tensile strength, and increase flexibility, elongation, impact strength, and tear strength of a polymeric resin (typically a thermoplastic polymer) to which it is added. A plasticizer may also lower the melting point of the polymeric resin, which lowers the glass transition temperature and enhances processability of the polymeric resin to which it is added. In an embodiment, the present plasticizer is a phthalate-free plasticizer, or is otherwise void or substantially void of phthalate.

The plasticizer includes an epoxidized fatty acid alkyl ester. The alkyl moiety of the ester may be, for example, a methyl group, an ethyl group, a propyl group, or a 2-ethylhexyl group. In an embodiment, the epoxidized fatty acid alkyl ester is an epoxidized fatty acid methyl ester (or "eFAME"). An "epoxidized fatty acid methyl ester" is a $C_4$-$C_{24}$ (saturated or unsaturated) carboxylic acid methyl ester with at least one epoxide group. An "epoxide group" is a three-member cyclic ether (also called oxirane or an alkylene oxide) in which an oxygen atom is joined to each of two carbon atoms that are already bonded to each other. Epoxidation reactions are typically performed with percarboxylic acids or other peroxy compounds.

The present plasticizer also includes an epoxidized natural oil ("eNO"). A "natural oil," as used herein, is an oil composed of fatty acid triglycerides and derived from a microbe (algae, bacteria), a plant/vegetable, and/or a seed. In an embodiment, natural oil includes genetically-modified natural oil. In another embodiment, the natural oil excludes petroleum-derived oil. Non-limiting examples of suitable natural oils include beef tallow oil, canola oil, castor oil, corn oil, fish oil, linseed oil, palm oil, rapeseed oil, safflower oil, soybean oil, sunflower oil, tall oil, tung oil, and any combination thereof.

The term "epoxidized natural oil," as used herein, is a natural oil wherein at least one fatty acid moiety contains at least one epoxide group. Epoxidation may occur by way of reaction of the natural oil with percarboxylic acid and/or other peroxy compounds.

Non-limiting examples of suitable eNO include epoxidized algae oil, epoxidized beef tallow oil, epoxidized canola oil, epoxidized castor oil, epoxidized corn oil, epoxidized fish oil, epoxidized linseed oil, epoxidized palm oil, epoxidized rapeseed oil, epoxidized safflower oil, epoxidized soybean oil, epoxidized sunflower oil, epoxidized tall oil, epoxidized tung oil, and any combination thereof.

In an embodiment, the epoxidized natural oil is an epoxidized soybean oil ("eSO").

In an embodiment, the plasticizer contains relative amounts of eNO (e.g., eSO) to eFAAE (e.g., eFAME) in a weight ratio in the range of from greater than (">") 0:less than ("<") 100 to <100:>0, more typically from 10:90 to 90:10, more typically from 20:80 to 80:20, and even more typically from 30:70 to 70:30. Weight ratios are based on total weight of the plasticizer.

In an embodiment, the plasticizer can undergo one or more color-reducing treatment processes. Such color-reducing treatment processes include distillation, filtration, treatment with a peroxide, and mixtures of two or more thereof.

In an embodiment, the color-reducing treatment includes distilling the above-described eFAAE (e.g., eFAME) prior to combining it with the eNO. Conventional distillation techniques are employed. For example, distillation can be performed with a wiped film evaporator ("WFE") and a condenser. In an embodiment, the distillation is performed employing a WFE at a temperature ranging from 120 to 180° C., from 140 to 170° C., or from 150 to 160° C. The condenser can have a temperature of 20° C.

In an embodiment, the color-reducing treatment includes filtering at least a portion of the eNO, the eFAAE, and/or the blended plasticizer composition. Conventional filtration techniques are employed. Illustrative examples of suitable filter media include Magnesol D60™ (available from The Dallas Group of America, Inc), Pure Flow B80™ (available from Oil Dri Corporation of America), activated alumina (available from Sigma-Aldrich or Delta adsorbents), fuller's earth clay (available from Sigma-Aldrich), and perlite (e.g., PF60™, available from The Schundler Company). In an embodiment, the plasticizer or blended plasticizer is stirred with the filtration medium for a time (e.g., 60 minutes) at elevated temperature (e.g., 40° C.). As used herein, the term "elevated temperature" denotes any temperature greater than ambient temperature. Thereafter, the mixture is filtered using, for example, a 1 micrometer ("μm") filter paper over an 11 μm filter paper, applying vacuum to accelerate filtration.

In an embodiment, the color-reducing treatment includes contacting at least a portion of the eNO, the eFAAE, and/or the blended plasticizer composition with a peroxide. In various embodiments, the plasticizer or plasticizer blend can be treated with peroxide solution at a concentration of from 1 to 3 wt % based on the combined weight of the peroxide solution and plasticizer. The mixture can then be stirred for a time (e.g., 60 minutes). The peroxide can be any peroxide known in the art. Peroxides generally have a structure $R^1OOR^2$, where $R^1$ and $R^2$ can be the same or different, and can be hydrogen, aliphatic, or aromatic groups. In various embodiments, the peroxide solution can be hydrogen peroxide ("$H_2O_2$"). The peroxide solution can be, for example, a 30% by weight aqueous solution.

In various embodiments, the eFAAE (e.g., eFAME) of the treated plasticizer comprises fatty acid dimers in a concentration of less than 0.1, less than 0.05, or less than 0.02 weight percent based on the entire weight of the eFAAE. Fatty acid dimer content can be determined by chromatographic analyses, as described in the Test Procedures below. Fatty acid dimers include molecules having two combined fatty acid aliphatic chains. The fatty acid aliphatic chains can be saturated, unsaturated, and/or epoxidized. Non-limiting examples of fatty acid dimers include molecules having structures such as:

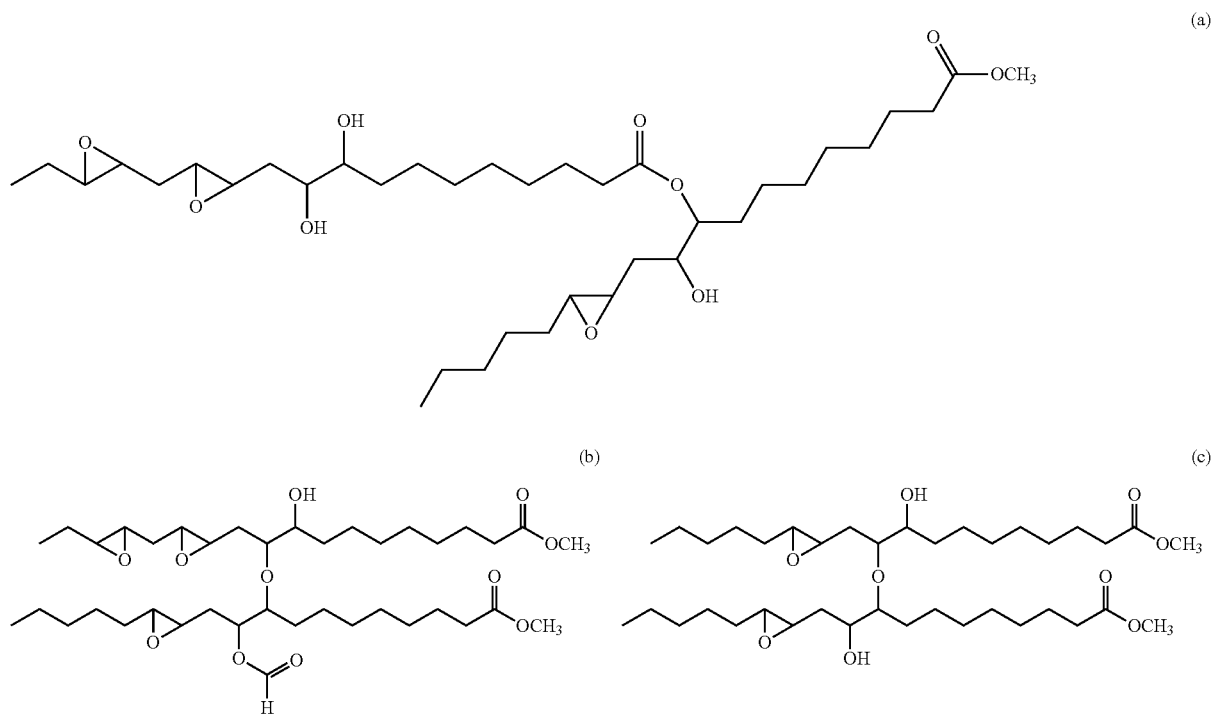

-continued

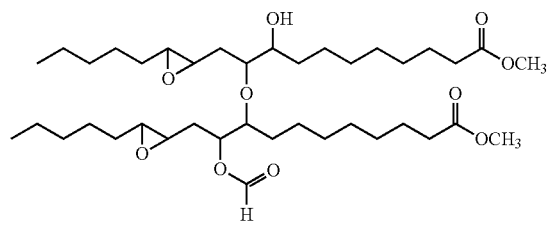
(d)

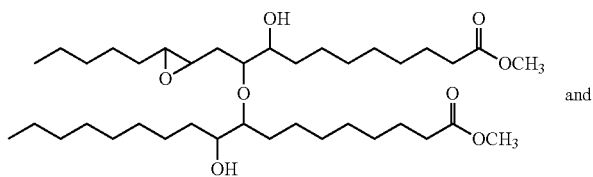
(e)
and

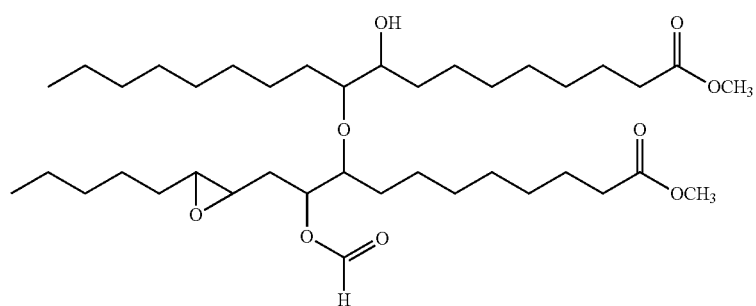
(f)

In various embodiments, the eFAAE (e.g., eFAME) of the treated plasticizer comprises fatty acid trimers in a concentration of less than 0.1, less than 0.05, or less than 0.02 weight percent based on the entire weight of the eFAAE. Fatty acid trimer content can be determined by chromatographic analyses, as described in the Test Procedures below.

Fatty acid trimers include molecules having three combined fatty acid aliphatic chains (e.g., triglycerides). The fatty acid aliphatic chains can be saturated, unsaturated, and/or epoxidized. Non-limiting examples of fatty acid trimers include molecules having structures such as:

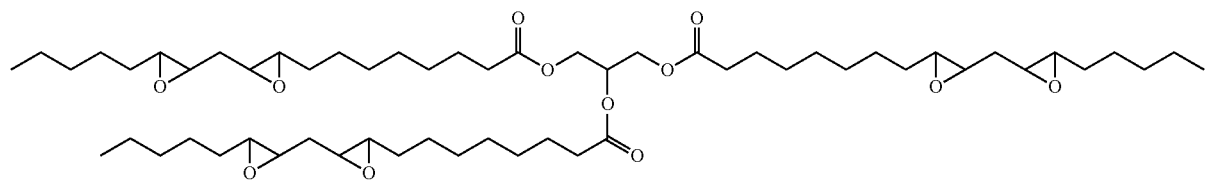
(g)

(h)

(i)

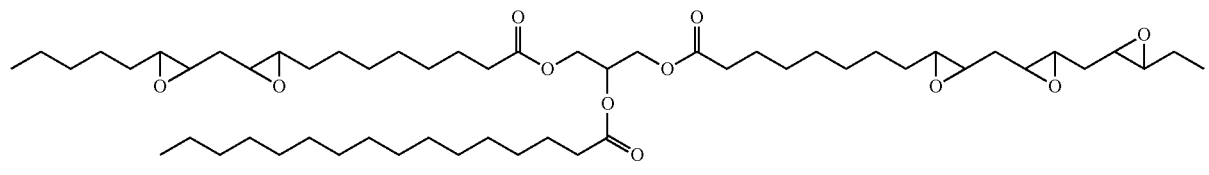
(j)

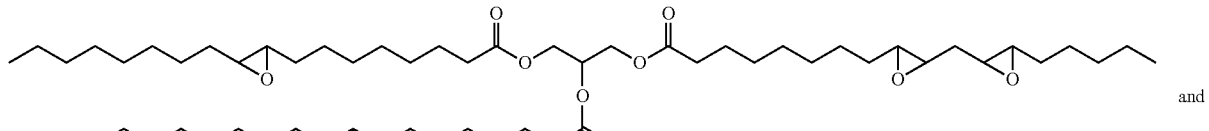

(k)

and

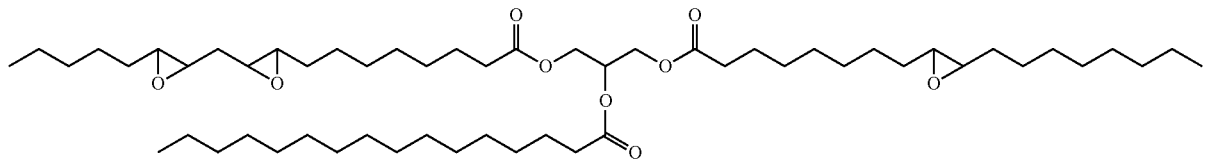

(l)

In various embodiments, the eFAAE (e.g., eFAME) of the treated plasticizer comprises a combined concentration of fatty acid dimers and fatty acid trimers in total amount of less than 0.1, less than 0.05, or less than 0.02 weight percent based on the entire weight of the eFAAE.

In various embodiments, the treated eFAAE, the treated eNO, and/or the treated combination thereof can have an American Public Health Association ("APHA") color index value of less than 100, less than 90, less than 80, less than 70, less than 60, less than 50, less than 40, or less than 30 upon heat aging at 190° C. for 60 minutes. Heat aging is performed according to the procedure described in the following Examples. APHA color is determined according to ASTM standards E1209 and E313.

Polymeric Composition

The present disclosure provides a polymeric composition. In an embodiment, a polymeric composition is provided which includes a polymeric resin and the present plasticizer as disclosed above.

Non-limiting examples of suitable polymeric resins include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, EPDM rubber, propylene-based polymers, ethylene-based polymers, and vinyl chloride resins. The term, "propylene-based polymer," as used herein, is a polymer that comprises a majority weight percent polymerized propylene monomer (based on the total amount of polymerizable monomers), and optionally may comprise at least one polymerized comonomer. The term, "ethylene-based polymer," as used herein, is a polymer that comprises a majority weight percent polymerized ethylene monomer (based on the total weight of polymerizable monomers), and optionally may comprise at least one polymerized comonomer.

The term "vinyl chloride resin," as used herein, is a vinyl chloride polymer, such as polyvinyl chloride ("PVC"), or a vinyl chloride copolymer such as vinyl chloride/vinyl acetate copolymer, vinyl chloride/vinylidene chloride copolymer, vinyl chloride/ethylene copolymer or a copolymer prepared by grafting vinyl chloride onto ethylene/vinyl acetate copolymer. The vinyl chloride resin can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer or acrylonitrile-butadiene-styrene polymer.

In an embodiment, the vinyl chloride resin is PVC.

In an embodiment, the polymeric composition includes from 40 wt % to 50 wt % PVC, from 5 wt % to 20 wt % eFAAE, from 5 wt % to 20 wt % eNO, and from greater than 0 wt % to 35 wt % filler.

Additives

The polymeric composition may include one or more of the following optional additives: a filler, a flame retardant, a heat stabilizer, an anti-drip agent, a colorant, a lubricant, a low molecular weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, and any combination thereof.

In an embodiment, the polymeric composition includes PVC, the present plasticizer, a filler (calcium carbonate, clays, silica, and any combination thereof), metal soap stabilizers (zinc stearate or mixed metal stabilizers containing Ca, Zn, Mg, Sn, and any combination thereof), a phenolic or related antioxidant, and a processing aid.

Coated Conductor

The present disclosure provides a coated conductor. The coated conductor includes a conductor and a coating on the conductor, the coating formed from the polymeric composition described above.

A "conductor," as used herein, is one or more wire(s) or fiber(s) for conducting heat, light, and/or electricity. The conductor may be a single-wire/fiber or a multi-wire/fiber and may be in strand form or in tubular form. Non-limiting examples of suitable conductors include metals such as silver, gold, copper, carbon, and aluminum. The conductor may also be optical fiber made from either glass or plastic.

The coated conductor may be flexible, semi-rigid, or rigid. The coating (also referred to as a "jacket" or a "sheath" or "insulation") is on the conductor or on another polymeric layer around the conductor.

Definitions

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone;

A and B in combination; A and C in combination; B and C in combination; or A, B, and C in combination.

"Natural oil" means an oil derived from one or more biological sources (e.g., seeds, vegetables, fish, animal fats, bacteria, or algae), as opposed to an oil derived from petroleum or other mineral source.

"Epoxidation" means a process of forming an epoxide, also known as an oxirane or alkylene oxide.

"Fatty acid" means a carboxylic acid composed of an aliphatic chain typically containing 4 to 24 carbon atoms with a terminal carboxyl group (—COOH). The fatty acid can be saturated or unsaturated, branched or unbranched, and may or may not include one or more hydroxyl group(s).

"Epoxidized fatty acid ester" means a compound with at least one fatty acid ester moiety which contains at least one epoxide group.

"Wire" means a single strand of conductive metal, e.g., copper or aluminum, or a single strand of optical fiber.

"Cable" means at least one wire or optical fiber within a sheath (e.g., an insulation covering or a protective outer jacket). Typically, a cable is two or more wires or optical fibers bound together, typically in a common insulation covering and/or protective jacket. The individual wires or fibers inside the sheath may be bare, covered or insulated. Combination cables may contain both electrical wires and optical fibers. The cable can be designed for low, medium, and/or high voltage applications. Typical cable designs are illustrated in U.S. Pat. Nos. 5,246,783, 6,496,629 and 6,714,707.

TEST METHODS

APHA Color Measurement

Measure liquid color according to ASTM standards E1209 and E313 using a BYK Gardner LCS III™ instrument and measure in APHA units. Set up the bench-top instrument and perform calibration check to insure the instrument is working within specifications. Measure sample color using the protocol listed below:
- Set LCS III to measure Hazen/Alpha indices;
- Measure each sample via syringe (10 mL) into individual calibrated cuvettes;
- Place each loaded cuvette into the LCS III and press the test button; a Hazen/Alpha number is generated. Record this number, remove the sample and place back into the LCS III to measure a second time (record data). Repeat for a third time (record data).
- Remove the loaded cuvette and set aside; reset the LCS III to measure Yellowness Index, measure the same cuvette for Yellowness Index (record three measurements).

Heat Aging

Heat each plasticizer sample in a type II convection oven at 190° C. Collect samples at time intervals indicated in the following Examples and rest on a table top to cool. After 24 hours, measure APHA values of each sample.

Distillation

Distillation Method for eFAME: Samples 1a-e

Employing a 2 inch molecular still, degas the sample under the following conditions:

TABLE 1

| Degassing (Pass 1): | |
| --- | --- |
| Wiped Film Evaporator ("WFE") Temperature (° C.) | 120 |

TABLE 1-continued

| Degassing (Pass 1): | |
| --- | --- |
| System Pressure (Torr) | 8.000 |
| Condenser Temp. (° C.) | 15 |
| Wiper Speed (rpm) | 400 |
| Distillate Recovered (g) | 0.0 |
| Residue Recovered (g) | 975.0 |
| Total Recovered (g) | 975.0 |
| Sampling Time (min.) | 140 |
| Feed Rate (g/hr.) | 418 |
| Distillate Recovered (wt %) | 0.0 |
| Residue Recovered (wt %) | 100.0 |

Use the residue stream from Pass 1 as feed for the distillation in Pass 2.

TABLE 2

| Distillation (Pass 2): | | | | | |
| --- | --- | --- | --- | --- | --- |
| Sample: | 1a | 1b | 1c | 1d | 1e |
| WFE Temperature (° C.) | 150 | 160 | 170 | 140 | 145 |
| System Pressure (Torr) | 0.035 | 0.035 | 0.035 | 0.035 | 0.035 |
| Condenser Temp. (° C.) | 20 | 20 | 20 | 20 | 20 |
| Wiper Speed, rpm | 400 | 400 | 400 | 400 | 400 |
| Distillate Recovered (g) | 105.0 | 138.0 | 111.0 | 80.0 | 101.0 |
| Residue Recovered (g) | 40.0 | 25.0 | 6.0 | 100.0 | 40.0 |
| Total Recovered (g) | 145.0 | 163.0 | 117.0 | 180.0 | 141.0 |
| Sampling Time (min.) | 20 | 25 | 20 | 28 | 26 |
| Feed Rate (g/hr.) | 435 | 391 | 351 | 386 | 325 |
| Distillate Recovered (wt %) | 72.4 | 84.7 | 94.9 | 44.4 | 71.6 |
| Residue Recovered (wt %) | 27.6 | 15.3 | 5.1 | 55.6 | 28.4 |

Distillation Method for TeFAME: Samples 2a-e

Employing a 2 inch molecular still, degas the sample under the following conditions:

TABLE 3

| Degassing (Pass 1): | |
| --- | --- |
| WFE Temperature (° C.) | 120 |
| System Pressure (Torr) | 8.000 |
| Condenser Temp. (° C.) | 15 |
| Wiper Speed (rpm) | 400 |
| Distillate Recovered (g) | 3.0 |
| Residue Recovered (g) | 980.0 |
| Total Recovered (g) | 983.0 |
| Sampling Time (min.) | 110 |
| Feed Rate (g/hr) | 536 |
| Distillate Recovered (wt %) | 0.3 |
| Residue Recovered (wt %) | 99.7 |

Use the residue stream from Pass 1 as feed for the distillation in Pass 2.

TABLE 4

| Distillation (Pass 2): | | | | | |
| --- | --- | --- | --- | --- | --- |
| Sample: | 2a | 2b | 2c | 2d | 2e |
| WFE Temperature (° C.) | 140 | 145 | 150 | 160 | 170 |
| System Pressure (Torr) | 0.063 | 0.065 | 0.064 | 0.067 | 0.065 |
| Condenser Temp. (° C.) | 20 | 20 | 20 | 20 | 20 |
| Wiper Speed (rpm) | 400 | 400 | 400 | 400 | 400 |
| Distillate Recovered (g) | 143.0 | 154.0 | 122.0 | 145.0 | 148.0 |
| Residue Recovered (g) | 37.0 | 33.0 | 13.0 | 10.0 | 7.0 |
| Total Recovered (g) | 180.0 | 187.0 | 135.0 | 155.0 | 155.0 |
| Sampling Time (min.) | 22 | 22 | 17 | 19 | 20 |

TABLE 4-continued

| Distillation (Pass 2): | | | | | |
|---|---|---|---|---|---|
| Sample: | 2a | 2b | 2c | 2d | 2e |
| Feed Rate (g/hr.) | 491 | 510 | 476 | 489 | 465 |
| Distillate Recovered (wt %) | 79.4 | 82.4 | 90.4 | 93.5 | 95.5 |
| Residue Recovered (wt %) | 20.6 | 17.6 | 9.6 | 6.5 | 4.5 |

Electrical Performance Testing

A Baur DTL C™ oil tester is used to measure electrical performance. Before testing each fluid, the dielectric test cell is thoroughly cleaned with Heptane. The empty cell is then calibrated to obtain the empty cell capacitance and check for contamination. The cell is filled with the test fluid and heated to the appropriate test temperature, typically 25° C. The $\varepsilon_r$ and tan δ are measured first according to ASTM D924, in which the test voltage is 2000 V (1000V/mm). The direct current resistivity is measured after $\varepsilon_r$/tan δ so as to prevent any effects of polarization on the following measurements. The resistivity is measured per ASTM D1169, in which 500 V of positive polarity is first applied and the resistivity measured followed by a discharging of the cell and subsequent measurement with negative polarity. The data is then reported as an average of the two readings.

Chromatographic Analyses

The samples were analyzed using a gas chromatography ("GC") system with the following conditions:
  Instrument: Agilent 6890 GC™
  Column: RTx-Biodiesel TG™ (Restek), 15 m×0.32 mm×0.1-μm film
  Injection: Split, Restek precision double wool liner
  Injection Volume: 1.0 μL
  Detection: flame ionization (FID)
  Carrier Gas: He
  Carrier Pressure: 8 psi, constant pressure
  Split flow: 123 mL/min
  Split ratio: 40
  Hydrogen: 30 mL/min
  Air: 350 mL/min
  Makeup: 25 mL/min
  Injector Temp: 340° C.
  Detector Temp: 350° C.
  Temperature Program: Initial Temp: 60° C. for 1 min.
  Ramp Rate: 15° C./min
  Final Temp: 350° C. for 20 min
  Data System: Thermo Atlas v 8.2

Filtration

With a sample size of 100 mL, stir the sample with the filtration medium for 60 minutes at 40° C. Thereafter, filter the solution using a 1 micrometer ("μm") filter paper over an 11 μm filter paper, applying vacuum to accelerate filtration. Filtration media are as follows:
  Magnesol D-60™ (available from the Dallas Group of America, Inc.)—synthetic magnesium silicate.
  Pure Flow B-80™ bleaching clay (available from Oil Dri Corporation of America)—mixture of montmorillonite type clay with fuller's earth clay and small levels of quartz.
  Activated alumina (available from Sigma-Aldrich)—alumina, highly porous with surface area over 200 m$^2$/g. Produced from aluminum hydroxide.
  Fuller's earth clay (available from Sigma-Aldrich)—extraction: 100% naturally occurring quarry mined (intergrowth of hormite and smectite minerals). Typical mineral content: silica (70.85%); sapphire crystal (14.06%); magnesium oxide (5.71%); iron oxide (5.34%), calcium oxide (1.62%).
  Perlite PF-60™ (available from The Schundler Company)—Perlite is essentially an amorphous, hydrated glassy volcanic rock of rhyolitic composition, consisting primarily of fused sodium potassium aluminum silicate.

Peroxide Treatment

As indicated below, add either 1 or 3 wt % of 30% hydrogen peroxide ($H_2O_2$) solution to the neat plasticizer sample and stir for about 60 minutes with a magnetic stir bar and stirrer. Weight percent of hydrogen peroxide is based on the combined weight of the neat plasticizer sample and the hydrogen peroxide. Perform reaction in a jar.

EXAMPLES

Example 1—Initial Color Analyses of Distilled Samples

Sample 1 Comp is an undistilled eFAME comparative sample. Distill eFAME Samples 1a through 1e according to procedure outlined above. Prior to distillation, the epoxidized samples are prepared according to the following general procedure for epoxidation. If the starting raw material is a fatty acid methyl ester ("FAME"), then epoxidation leads to eFAME; if the starting raw material is soybean oil, then epoxidation leads to ESO.

Typically ester or soybean oil, peroxide, and formic acid are combined in 1:2:0.5 proportions, respectively. 50 g of ester (or soybean oil) and corresponding amount of formic acid are weighed in a 3-necked round-bottomed flask ("RBF") equipped with a mechanical stirrer, condenser and a dropper for controlled addition of $H_2O_2$. The mixture of ester and formic acid are stirred at a speed of 400 rpm at 30° C. Calculated amount of hydrogen peroxide (30 or 50 wt %) is added at the rate of 10 mL/hr and then slowly increasing the rate to the required flow rate depending on the exothermicity of the reaction. Addition is generally completed within an hour. The reaction temperature is then raised to 40 or 50° C. and the reaction is continued until the oxirane oxygen value does not increase further. Stirring is stopped and layers are separated. Oil layer is first washed with water followed by dilute potassium hydroxide and again with water or brine. The oil layer is then dried under vacuum.

Sample 2 Comp is an undistilled TeFAME comparative sample. Distill TeFAME Samples 2a through 2e according to the procedure outlined above. The TeFAME samples are prepared according to the following general procedure. Oleic acid (60 g), methanol or any other alcohol (33.92 g), and sulfuric acid (1 wt % of acid, 0.6 g) are weighed in a 2 necked RBF equipped with condenser and temperature sensor. The reaction mixture is heated in an oil batch at 65° C. under nitrogen flow for 6 hours. In some reactions water may form during the reaction, which can be azeotropically removed using toluene. After the reaction, the mixture is washed with water and potassium carbonate to remove unreacted oleic acid, followed by wash with water or brine. Excess alcohol is removed using a rotary evaporator. The final product is dried under vacuum.

Following distillation, analyze each sample for color according to the procedure outlined above.

TABLE 5

Initial Color of Distilled Samples

| Sample | WFE Temperature (° C.) | Average Color (APHA) | Std. Dev. |
|---|---|---|---|
| 1 Comp | — | 8 | 1 |
| 1a | 150 | 4 | 1 |
| 1b | 160 | 4 | 2 |
| 1c | 170 | 6 | 1 |
| 1d | 140 | 3 | 1 |
| 1e | 145 | 3 | 2 |
| 2 Comp | — | 249 | 1 |
| 2a | 140 | 18 | 0 |
| 2b | 145 | 19 | 1 |
| 2c | 150 | 22 | 2 |
| 2d | 160 | 31 | 2 |
| 2e | 170 | 41 | 1 |

Example 2—Heat Aged Color Analyses of Distilled Samples

Heat age each sample as prepared in Example 1 according to the heat aging procedure outlined above. Analyze each sample for color according to the procedure outlined above.

TABLE 6

Heat Aged Color of Distilled Samples

| Sample | WFE Temperature (° C.) | Heat Aging (@190° C.) Time (min.) | Average Color (APHA) | Std. Dev. |
|---|---|---|---|---|
| 1 Comp | — | 0 | 8 | 1 |
| 1 Comp | — | 10 | 10 | 1 |
| 1 Comp | — | 25 | 11 | 1 |
| 1 Comp | — | 45 | 32 | 2 |
| 1 Comp | — | 60 | 112 | 1 |
| 1a | 150 | 0 | 4 | 1 |
| 1a | 150 | 10 | 7 | 1 |
| 1a | 150 | 25 | 10 | 1 |
| 1a | 150 | 45 | 15 | 1 |
| 1a | 150 | 60 | 37 | 1 |
| 1b | 160 | 0 | 4 | 2 |
| 1b | 160 | 10 | 6 | 1 |
| 1b | 160 | 25 | 11 | 1 |
| 1b | 160 | 45 | 18 | 2 |
| 1b | 160 | 60 | 48 | 1 |
| 1c | 170 | 0 | 6 | 1 |
| 1c | 170 | 10 | 9 | 1 |
| 1c | 170 | 25 | 16 | 2 |
| 1c | 170 | 60 | 78 | 1 |
| 1d | 140 | 0 | 3 | 1 |
| 1d | 140 | 10 | 7 | 1 |
| 1d | 140 | 25 | 10 | 2 |
| 1d | 140 | 45 | 13 | 1 |
| 1d | 140 | 60 | 27 | 1 |
| 1e | 145 | 0 | 3 | 2 |
| 1e | 145 | 10 | 10 | 1 |
| 1e | 145 | 25 | 8 | 1 |
| 1e | 145 | 45 | 14 | 2 |
| 1e | 145 | 60 | 22 | 1 |
| 2 Comp | — | 0 | 249 | 1 |
| 2 Comp | — | 10 | 305 | 1 |
| 2 Comp | — | 25 | 469 | 1 |
| 2 Comp | — | 45 | 746 | 1 |
| 2 Comp | — | 60 | 1000 | 0 |
| 2a | 140 | 0 | 18 | 0 |
| 2a | 140 | 10 | 19 | 1 |
| 2a | 140 | 25 | 22 | 2 |
| 2a | 140 | 45 | 24 | 1 |
| 2a | 140 | 60 | 25 | 0 |
| 2b | 145 | 0 | 19 | 1 |
| 2b | 145 | 10 | 18 | 1 |
| 2b | 145 | 25 | 25 | 1 |
| 2b | 145 | 45 | 23 | 2 |
| 2b | 145 | 60 | 27 | 1 |
| 2c | 150 | 0 | 22 | 2 |
| 2c | 150 | 10 | 21 | 1 |
| 2c | 150 | 25 | 25 | 1 |
| 2c | 150 | 45 | 32 | 1 |
| 2c | 150 | 60 | 33 | 1 |
| 2d | 160 | 0 | 31 | 2 |
| 2d | 160 | 10 | 30 | 1 |
| 2d | 160 | 25 | 40 | 1 |
| 2d | 160 | 45 | 56 | 1 |
| 2d | 160 | 60 | 56 | 2 |
| 2e | 170 | 0 | 41 | 1 |
| 2e | 170 | 10 | 43 | 1 |
| 2e | 170 | 25 | 51 | 1 |
| 2e | 170 | 45 | 90 | 2 |
| 2e | 170 | 60 | 85 | 2 |

All distilled samples show decreased color upon heat aging as compared to undistilled control samples, particularly at longer aging times (e.g., 60 minutes).

Example 3—Electrical Performance of Distilled Samples

Analyze each sample as prepared in Example 1 according to the electrical performance testing procedure outlined above.

TABLE 7

Electrical Performance of Distilled Samples

| Sample | Insulation Resistance (Rho+) | Insulation Resistance (Rho−) | Test Voltage (V) | Test Temp (° C.) |
|---|---|---|---|---|
| 1 Comp | 6.67E+07 | 6.14E+07 | 500 | 25.2 |
| 1a | 3.00E+08 | 3.29E+08 | 500 | 25.3 |
| 1b | 1.94E+08 | 2.15E+08 | 499.8 | 25.2 |
| 1c | 1.03E+08 | 1.07E+08 | 499.8 | 25.1 |
| 1d | 5.11E+08 | 5.45E+08 | 500 | 25.3 |
| 1e | 3.02E+08 | 3.24E+08 | 499.8 | 25.3 |
| 2 Comp | 1.64E+08 | 1.66E+08 | 499.8 | 25.6 |
| 2a | 4.44E+08 | 4.64E+08 | 499.8 | 25.1 |
| 2b | 5.11E+08 | 5.14E+08 | 499.8 | 25.2 |
| 2c | 3.26E+08 | 3.32E+08 | 500 | 25.3 |
| 2d | 2.06E+08 | 2.10E+08 | 500 | 25.2 |
| 2e | 1.54E+08 | 1.56E+08 | 499.8 | 25.5 |

Distillation of the eFAME and TeFAME samples increased insulation resistance in all samples except for 2e.

Example 4—Chromatographic Analyses of Distilled and Control eFAME Samples

Prepare samples for injection as follows: weigh 100 μL of sample and 100 μL of pentadecane internal standard into a vial. Add approximately 5 mL of tetrahydrofuran ("THF") and mix the resulting solution thoroughly. Place an aliquot of this solution in a 2-mL autosampler vial and analyze using the GC conditions and Samples 1 Comp and 1a-e, described above.

TABLE 8

Chromatographic Analyses of Distilled and Control eFAME Samples

| Sample Name | Palmitate (wt %)[a] | Stearate (wt %) | Monoepoxy (wt %) | Diepoxy (wt %) | Triepoxy (wt %) | Dimers (wt %) | Total |
|---|---|---|---|---|---|---|---|
| 1 Comp | 10.69 | 4.60 | 22.51 | 49.03 | 8.63 | 0.53 | 95.98 |
| Residue Sample 1a | 0.18 | 0.10 | 3.85 | 55.34 | 22.66 | 2.74 | 84.87 |
| Residue Sample 1b | 0.05 | 0.08 | 2.40 | 28.49 | 32.05 | 7.99 | 71.06 |
| Residue Sample 1c | 0.04 | 0.07 | 2.19 | 19.32 | 24.36 | 16.48 | 62.46 |
| Residue Sample 1d | 0.02 | 0.25 | 13.79 | 60.76 | 12.99 | 1.28 | 89.09 |
| Residue Sample 1e | 0.01 | 0.04 | 4.76 | 55.01 | 21.25 | 2.62 | 83.69 |
| Distillate Sample 1a | 15.10 | 5.83 | 29.25 | 45.50 | 2.84 | n.d.[b] | 98.53 |
| Distillate Sample 1b | 12.19 | 4.73 | 24.55 | 49.71 | 4.91 | n.d. | 96.09 |
| Distillate Sample 1c | 11.45 | 4.44 | 23.16 | 49.06 | 6.45 | n.d. | 94.54 |
| Distillate Sample 1d | 25.19 | 9.46 | 34.37 | 31.84 | 1.35 | n.d. | 102.21 |
| Distillate Sample 1e | 15.63 | 5.98 | 29.34 | 44.59 | 2.55 | n.d. | 98.08 |

[a]Weight percents reported as an average of two injections
[b]Not detected

Example 5—Initial Color Analyses of Filtered Samples

Employing a blend of ESO and eFAME plasticizers, each prepared according to the procedure outlined in Example 1, prepare five filtered samples according to the procedure outlined above and employing the following weight ratios:

TABLE 9

Filtered Sample Preparation

| Sample: | 3a | 3b | 3c | 3d | 3e |
|---|---|---|---|---|---|
| ESO | 47.5 | 47.5 | 47.5 | 47.5 | 47.5 |
| eFAME | 47.5 | 47.5 | 47.5 | 47.5 | 47.5 |
| Magnesol D60 | 5 | — | — | — | — |
| Pure Flow B-80 | — | 5 | — | — | — |
| Activate alumina | — | — | 5 | — | — |
| Fuller's earth clay | — | — | — | 5 | — |
| Perlite PF-60 | — | — | — | — | 5 |

Analyze each sample for color according to the procedure outlined above. Sample 3 Comp is an unfiltered comparative sample with a 50/50 wt/wt blend of ESO and eFAME.

TABLE 10

Initial Color of Filtered Samples

| Sample | Color (APHA) |
|---|---|
| 3 Comp | 44 |
| 3a | 30 |
| 3b | 40 |
| 3c | 32 |
| 3d | 65 |
| 3e | 54 |

Samples treated with Magnesol D 60™, Pure Flow B-80™ and activated alumina show a decline in initial color.

Example 6—Heat Aged Color Analyses of Filtered Samples

Heat age each sample as prepared in Example 5 according to the heat aging procedure outlined above. Analyze each sample for color according to the procedure outlined above.

TABLE 11

Heat Aged Color of Filtered Samples

| Sample | Heat Aging (@190° C.) Time (min.) | Average Color (APHA) | Std. Dev. | Percent Increase in Color upon Aging (%) |
|---|---|---|---|---|
| 3 Comp | 0 | 44 | 2 | 0 |
| 3 Comp | 10 | 54 | 1 | 24 |
| 3 Comp | 15 | 74 | 2 | 70 |
| 3 Comp | 25 | 91 | 4 | 108 |
| 3 Comp | 40 | 209 | 2 | 379 |
| 3 Comp | 60 | 410 | 1 | 840 |
| 3 Comp | 80 | 562 | 3 | 1187 |
| 3 Comp | 100 | 577 | 3 | 1221 |
| 3a | 0 | 22 | 3 | 0 |
| 3a | 10 | 26 | 2 | 16 |
| 3a | 25 | 19 | 1 | −15 |
| 3a | 40 | 61 | 3 | 172 |
| 3a | 60 | 341 | 1 | 1428 |
| 3a | 90 | 445 | 1 | 1894 |
| 3a | 120 | 536 | 1 | 2299 |
| 3b | 0 | 31 | 7 | 0 |
| 3b | 10 | 36 | 2 | 17 |
| 3b | 25 | 38 | 1 | 24 |
| 3b | 40 | 64 | 4 | 108 |
| 3b | 60 | 314 | 1 | 912 |
| 3b | 90 | 437 | 1 | 1309 |
| 3b | 120 | 549 | 2 | 1671 |
| 3c | 0 | 30 | 1 | 0 |
| 3c | 10 | 29 | 1 | −2 |

TABLE 11-continued

Heat Aged Color of Filtered Samples

| Sample | Heat Aging (@190° C.) Time (min.) | Average Color (APHA) | Std. Dev. | Percent Increase in Color upon Aging (%) |
|---|---|---|---|---|
| 3c | 25 | 29 | 1 | −3 |
| 3c | 40 | 61 | 6 | 102 |
| 3c | 60 | 303 | 1 | 909 |
| 3c | 90 | 447 | 3 | 1390 |
| 3c | 120 | 581 | 2 | 1837 |
| 3d | 0 | 61 | 1 | 0 |
| 3d | 10 | 63 | 2 | 3 |
| 3d | 25 | 61 | 1 | 0 |
| 3d | 40 | 97 | 1 | 59 |
| 3d | 60 | 365 | 1 | 495 |
| 3d | 90 | 546 | 0 | 790 |
| 3d | 120 | 674 | 4 | 998 |
| 3e | 0 | 52 | 2 | 0 |
| 3e | 10 | 53 | 1 | 2 |
| 3e | 25 | 54 | 3 | 3 |
| 3e | 40 | 92 | 1 | 75 |
| 3e | 60 | 344 | 1 | 557 |
| 3e | 90 | 509 | 7 | 873 |
| 3e | 120 | 642 | 1 | 1126 |

All samples showed significant reduction in color formulation during elevated thermal aging cycle with up to 60% reduction in color after 40 minutes of aging at 190° C.

Example 7—Heat Aged Color Analyses of Peroxide-Treated Samples

Prepare the following samples according to the peroxide treatment described above. Samples 4 Comp, 5 Comp, and 6 Comp are left untreated as comparative samples. Weight percent of peroxide is based on combined weight of $H_2O_2$ solution and plasticizer.

TABLE 12

Peroxide-treated Sample Preparation

| Sample | Plasticizer type | Peroxide Treatment Amount (wt %) |
|---|---|---|
| 4 Comp | eFAME | — |
| 4a | eFAME | 1 |
| 4b | eFAME | 3 |
| 5 Comp | eFAME | — |
| 5 | eFAME | 1 |
| 6 Comp | ESO | — |
| 6 | ESO | 1 |

Heat age each sample according to the heat aging procedure outlined above. Analyze each sample for color according to the procedure outlined above.

TABLE 13

Heat Aged Color of Peroxide-treated Samples

| Sample | Heat Aging (@190° C.) Time (min.) | Average Color (APHA) | Std. Dev. | Percent Increase in Color upon Aging (%) |
|---|---|---|---|---|
| 4 Comp | 0 | 85 | 0 | 0 |
| 4 Comp | 10 | 95 | 3 | 11 |
| 4 Comp | 25 | 117 | 2 | 38 |
| 4 Comp | 40 | 143 | 1 | 69 |
| 4 Comp | 60 | 195 | 6 | 129 |
| 4 Comp | 90 | 264 | 4 | 211 |
| 4 Comp | 120 | 265 | 1 | 212 |
| 4a | 0 | 72 | 0 | 0 |
| 4a | 10 | 77 | 2 | 6 |
| 4a | 25 | 83 | 2 | 16 |
| 4a | 40 | 79 | 2 | 10 |
| 4a | 60 | 89 | 1 | 24 |
| 4a | 90 | 238 | 1 | 230 |
| 4a | 120 | 463 | 3 | 544 |
| 4b | 0 | 80 | 3 | 0 |
| 4b | 25 | 67 | 2 | −16 |
| 4b | 60 | 60 | 1 | −25 |
| 4b | 120 | 649 | 1 | 712 |
| 5 Comp | 0 | 11 | 2 | 0 |
| 5 Comp | 10 | 18 | 3 | 66 |
| 5 Comp | 15 | 25 | 1 | 137 |
| 5 Comp | 25 | 46 | 2 | 328 |
| 5 Comp | 40 | 135 | 1 | 1163 |
| 5 Comp | 60 | 294 | 4 | 2659 |
| 5 Comp | 80 | 441 | 1 | 4031 |
| 5 Comp | 100 | 460 | 1 | 4212 |
| 5 | 0 | 7 | 1 | 0 |
| 5 | 10 | 10 | 1 | 41 |
| 5 | 25 | 14 | 0 | 91 |
| 5 | 40 | 30 | 2 | 314 |
| 5 | 60 | 265 | 1 | 3518 |
| 5 | 90 | 561 | 2 | 7550 |
| 5 | 120 | 929 | 3 | 12568 |
| 6 Comp | 0 | 17 | 1 | 0 |
| 6 Comp | 10 | 22 | 5 | 31 |
| 6 Comp | 25 | 96 | 3 | 467 |
| 6 Comp | 40 | 243 | 2 | 1327 |
| 6 Comp | 60 | 658 | 2 | 3769 |
| 6 Comp | 90 | 1000 | 0 | 5782 |
| 6 Comp | 120 | 1000 | 0 | 5782 |
| 6 | 0 | 100 | 2 | 0 |
| 6 | 10 | 95 | 1 | −5 |
| 6 | 25 | 89 | 3 | −10 |
| 6 | 40 | 86 | 4 | −14 |
| 6 | 60 | 96 | 3 | −4 |
| 6 | 120 | 444 | 13 | 346 |

Color improvements can be seen during initial cycle of heat aging (i.e., up to 60 minutes) at 190° C. for samples 4a, 4b, and 5, in comparison to comparative samples 4 Comp and 5 Comp. Color improvements are seen over a longer period of the heat aging cycle for sample 6 in comparison to comparative sample 6 Comp.

The invention claimed is:

1. A method for producing a treated plasticizer, said method comprising:
   (a) combining a first plasticizer and a second plasticizer to thereby form a plasticizer composition, wherein said first plasticizer comprises epoxidized fatty acid alkyl esters, wherein said second plasticizer comprises an epoxidized natural oil; and (b) subjecting said first plasticizer, said second plasticizer, and/or said plasticizer composition to one or more color-reducing treatment processes to thereby produce said treated plasticizer, wherein said color-reducing treatment process is selected from the group consisting of:

(i) contacting at least a portion of said first plasticizer, said second plasticizer, and/or said plasticizer composition with a peroxide;

(ii) filtering at least a portion of said first plasticizer, said second plasticizer, and/or said plasticizer composition;

(iii) distilling at least a portion of said first plasticizer prior to said combining of step (a); and (iv) mixtures of two or more thereof, wherein said color-reducing treatment process comprises process (iii), wherein said distillation is performed at a temperature in the range of from 120 to 180° C.

2. The method of claim 1, wherein said epoxidized fatty acid alkyl esters are epoxidized fatty acid methyl esters, wherein said epoxidized natural oil is an epoxidized soybean oil.

3. The method of claim 1, wherein said color-reducing treatment process further comprises process (i), wherein said peroxide is hydrogen peroxide.

4. The method of claim 1, wherein said color-reducing treatment process further comprises process (ii), wherein said filtering is performed by passing at least a portion of said first plasticizer, said second plasticizer, and/or said plasticizer composition through a filter media selected from the group consisting of synthetic magnesium silicate, bleaching clay, montmorillonite clay, fuller's earth clay, activated alumina, perlite, and mixtures of two or more thereof.

5. The method of claim 1, wherein said first plasticizer has an APHA value of less than 100 upon heat aging at 190° C. for 60 minutes following said color-reducing treatment process.

6. The method of claim 1, wherein said plasticizer composition has an APHA value that is less than the APHA value of an identical reference plasticizer composition that has not undergone any of said color-reducing treatment processes of step (b) upon heat aging both said plasticizer composition and said reference plasticizer composition at 190° C. for 60 minutes.

* * * * *